United States Patent [19]
Fareed

[11] Patent Number: 5,865,782
[45] Date of Patent: Feb. 2, 1999

[54] KNEE COMPRESSION BAND

[76] Inventor: Donald O. Fareed, 801 Buena Vista Ave., Santa Barbara, Calif. 93108

[21] Appl. No.: 825,437

[22] Filed: Mar. 28, 1997

Related U.S. Application Data

[63] Continuation of Ser. No. 357,767, Dec. 16, 1994, abandoned, which is a continuation-in-part of Ser. No. 189,901, Feb. 1, 1994, abandoned.

[51] Int. Cl.$^6$ ....................................................... A61F 5/00
[52] U.S. Cl. ............................................... 602/62; 602/26
[58] Field of Search ................................. 602/5, 23, 26, 602/60–63, 78; 128/882, 898

[56] References Cited

U.S. PATENT DOCUMENTS

| | | | |
|---|---|---|---|
| 3,194,233 | 7/1965 | Peckham | 602/62 X |
| 3,926,186 | 12/1975 | Nirschl | 602/62 |
| 4,182,318 | 1/1980 | Beige et al. | 602/62 X |
| 4,334,528 | 6/1982 | Gauvry | 602/26 |
| 4,353,362 | 10/1982 | Demarco | 602/26 |
| 4,724,831 | 2/1988 | Huntjens | 602/26 |
| 4,777,946 | 10/1988 | Watanabe et al. | 602/62 |
| 4,872,448 | 10/1989 | Johnson, Jr. | 602/26 |
| 5,139,015 | 8/1992 | Morneau | 602/62 |

*Primary Examiner*—Linda C. M. Dvorak
*Attorney, Agent, or Firm*—Joseph L. Strabala

[57] ABSTRACT

A compression band for treating disorders of the knee, including arthritis, synovitis, chondromalacia patella, patella tendonitis, and the like. The band comprises a compressive member which generally has the profile of a bowtie or "dog bone," and an encircling strap portion which holds the compressive member in position on the knee. The compressive member is symetrically shaped so that it applies pressure to the medial and lateral infra-patellar retinaculum and inferior portion of the patellar tendon. This compression dampens the motion associated with the rapid acceleration/ deceleration of the soft tissue folds as they pass over the margins of the femoral condyles during flexion and extension of the leg. The compressive member serves as a shock absorber to prevent rapid acceleration and deceleration of the tissue as it passes over the condyle, thereby reducing microtrauma to the tissue and resultant inflammation. The compressive portion of the band is an arcuate plate having a parabolic, or "V" shaped, upper margin and a horizontal lower margin. The band permits the patellar tendon to change its angle without undue restriction during use. The compressive portion of the band is preferably a flexible plastic construction with an inner skin-contacting compressible portion. The compressible portion provides shock absorption in the event that the wearer falls down or suffers other trauma.

6 Claims, 5 Drawing Sheets

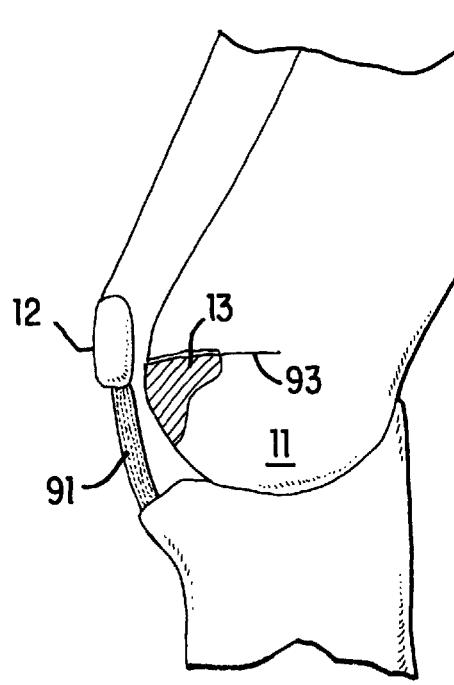 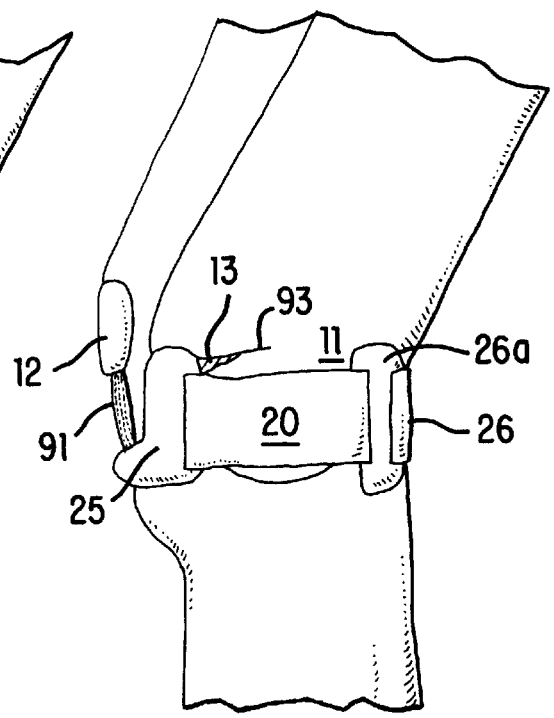
FIG.11(a)   FIG.11(b)
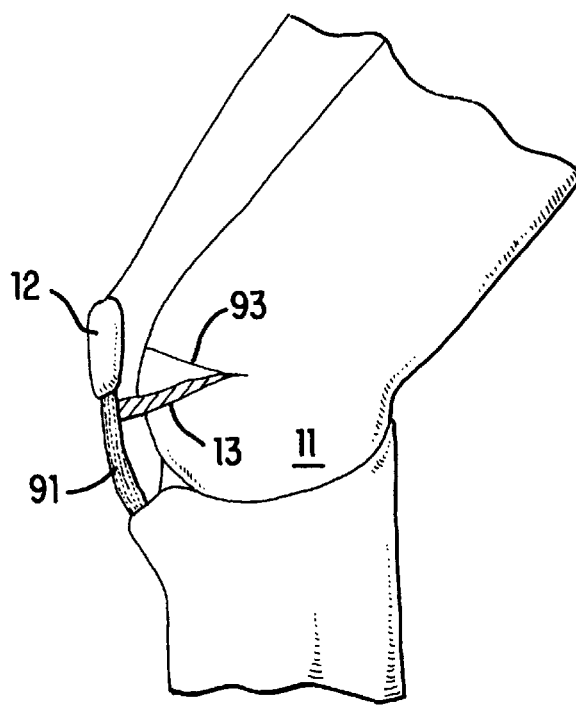 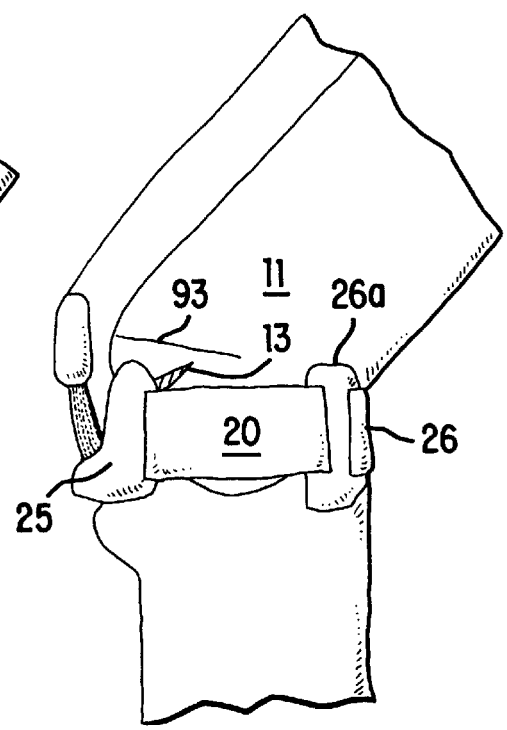
FIG.12(a)   FIG.12(b)

KNEE COMPRESSION BAND

This application is a continuation of U.S. Ser. No. 08/357,767 which was filed Dec. 16, 1994, now abandoned, which is a CIP of U.S. Ser. No. 08/189,901 filed Feb. 1, 1994, now abandoned.

BACKGROUND OF THE INVENTION

1. Field of the Invention

This invention relates in general to knee straps or braces useful for treating disorders of the knee, and more particularly to a compression band for treating soft tissue inflammation and patella-related disorders of the knee.

2. Prior Art

Chondromalacia of the patella is a common disorder and the result of normal motion of the patella with respect to the underlying femoral condyles. There have been a number of braces and straps devised to stabilize the patella and prevent such unwanted motion and to relieve the symptoms of chondromalacia patella.

Palumbo, in U.S. Pat. No. 4,370,978, issued Feb. 1st, 1983, and U.S. Pat. No. 4,296,744, issued Oct. 27, 1981, describes a brace suitable for treating certain patella-related disorders of the knee. The brace includes two para-patellar pads which function to stabilize the patella, an infra-patellar ligament pad which applies direct pressure to the patellar ligament, and a supra-patellar and an infra-patellar elastic strap which applies compressive force to the quadriceps mass and to the patellar ligament to diminish shock and compression and tensile forces to the extensor mechanism. The brace of Palumbo is substantially an elastic member with a circular region removed to overlie the patella. The construction of the brace is such that it restricts the motion of the leg and prevents the wearer from participating effectively in sports and the like. It is designed to stabilize the patella by splinting it. Moreover, the construction is such that, when the knee is bent, the compression of the popiteal region comprises a tourniquet, which further restricts the supply of blood to the lower extremity.

Gauvry, in U.S. Pat. No. 4,334,528, issued Jun. 15, 1982, describes yet another knee strap for treating chondromalacia patella and similar disorders. The Gauvry strap is substantially a section of surgical tubing which has been covered with a stockinet and encircles the leg so that the tubing overlies the patella thereby stabilizing it. The portion of the strap that directly overlies the patella is circular in cross-section and is narrower than the rest of the band. The band that fastens behind the knee is flat and wider than the front portion comprises a tourniquet when the knee is flexed. The pressure applied to the patellar tendon by the tubing is to prevent lateral motion of the patella during use. Beige, et al., U.S. Pat. No. 4,182,318 discloses a band useful for the treatment of epicondylitis. The band, dimensioned to encircle the elbow, comprises a pair of compression plates of unequal size which are in opposition to one another. The larger jaw engages the unaffected side of the inflicted elbow and, with its larger pressing surface, helps to prevent distortion of the underlying tissue. The smaller (opposing) jaw is dimensioned to apply more concentrated pressure on a smaller specific area. While the foregoing clamp is useful for treating epicondylitis, limitations presented by the asymmetry of the device limits its utility with respect to treating conditions of the knee. Nirschl, in U.S. Pat. No. 3,926,186, discloses a muscular support device for bracing muscles and tendons associated therewith. The device comprises a foam-backed cloth (canvas) wrap adapted for encircling the knee. The wrap applies circumferential pressure to the encircled underlying tissue. A portion of the wrap is contoured to avoid compressing the patella. The wrap is circumferential and supple, readily conforming to the contour of the underlying anatomy. The device necessarily applies circumferential compression to all of the underlying tissue; less pressure being exerted on the underlying skin where the skin-contacting surface of the wrap is larger and greater pressure where the skin-contacting surface is less. Thus, in operation, the wrap exerts a tourniquet effect, impairing the flow of blood to and from tissue distal to the knee.

In summary, prior art knee straps to treat problems associated with flexion and extension of the knee are directed toward stabilizing or splinting the patella to prevent the lateral displacement of the patella during activity. The present invention departs from the prior art in that it focuses on the motion of soft tissue over the femoral condyle during motion of the leg. The present invention teaches the use of a knee band for the treatment of flexion/extension-related disorders of the knee. The band has a compressive portion and a strap portion which holds the compressive portion in position. The band of the present invention is comfortable to wear and applies pressure only to those portions of the knee which are effective for preventing soft tissue microtrauma associated with the rapid acceleration/deceleration of the soft tissue folds of the knee during flexion and extension. The compressive portion of the band does not apply pressure to the patella and the strap portion is designed to minimize the tourniquet effect.

SUMMARY OF THE INVENTION

It is an object of this invention to provide a strap for providing relief for disorders of the knee associated with inflammation caused by flexion and/or extension of the leg.

It is still another object of the invention to provide a strap that can be worn around the knee during activity to reduce inflammation in soft tissue of the knee and yet permit substantially unimpeded use of the affected leg.

It is still another object of the invention to provide a strap for treating disorders of the knee involving flexion and/or extension which permits substantially unimpeded movement of the patellar ligament.

These and other objects of the invention will soon become apparent as we turn our attention now to the preferred embodiment of the invention.

BRIEF DESCRIPTION OF THE DRAWINGS

FIG. 11(a) is a lateral schematic view of a knee with about 20° of flexion.

FIG. 11(b) is a lateral schematic view of a knee with about 20° of flexion with the band of the present invention positioned to apply pressure to the synovial tissue lateral and posterior to the patella.

FIG. 12(a) is a lateral schematic view of a knee with about 30° of flexion.

FIG. 12(b) is a lateral schematic view of a knee with about 30° of flexion with the band of the present invention positioned to apply pressure to the synovial tissue lateral and posterior to the patella.

DESCRIPTION OF THE PREFERRED EMBODIMENT

Figure 1:
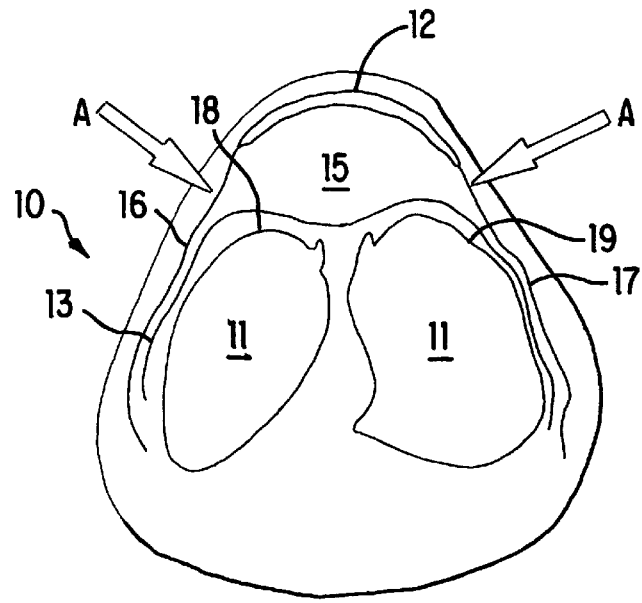
FIG. 1 shows a cross-sectional view through the middle of the knee in the region of the femoral condyles.

A cross-section through the middle of the knee in the region of the femoral condyles is shown in FIG. 1. The femoral condyles 11 are posterior to the patella 12 and are separated from the patella 12 by fat bodies 15 generally comprising adipose tissue. The patella 12 is held in position by the medial and lateral retinaculum shown at 16 and 17 respectively. The broad arrows A are directed medially towards the center of the knee to press on the medial and lateral patellar retinaculum 16 and 17 at the points where the soft synovial tissue 13 underlying the retinaculum rides across the medial and lateral margins 18 and 19 of the femoral condyle 11 during flexion.

Figure 2:
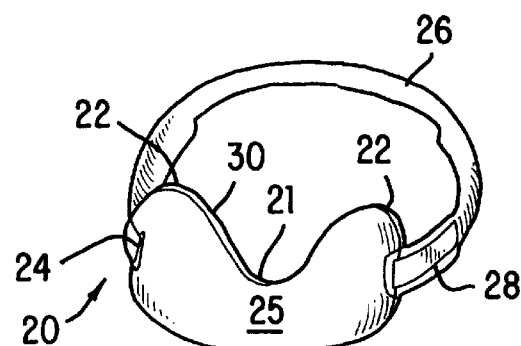
FIG. 2 is a plan view showing the general construction of the band of the present invention.
Figure 2A:
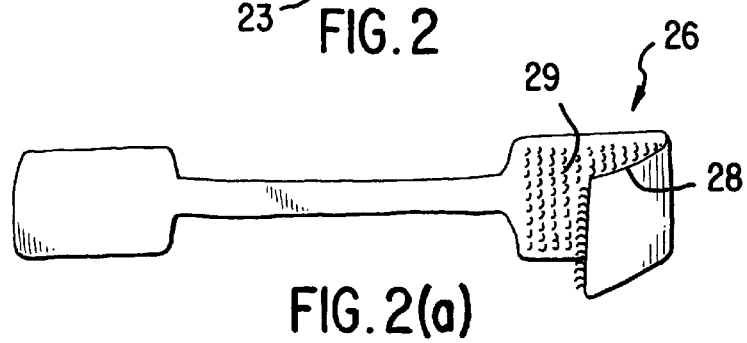
FIG. 2(a) is a perspective view showing the strap portion of the band of FIG. 2.
Figure 2B:
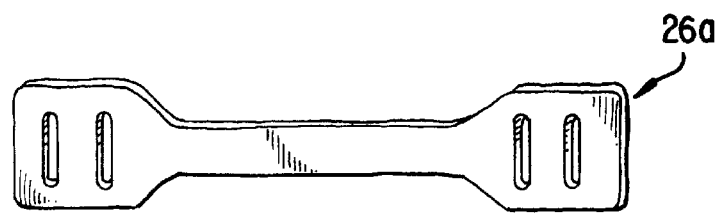
FIG. 2(b) is an optional compressive lining for the skin-contacting surface of the strap of FIG. 2(a).
Figure 3:
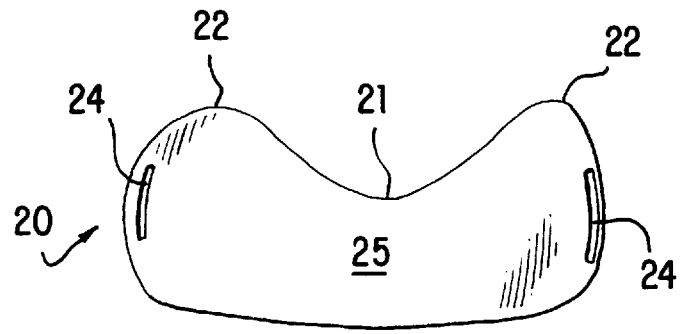
FIG. 3 is a front view of the compression plate portion of the band of the present invention.
Figure 3A:
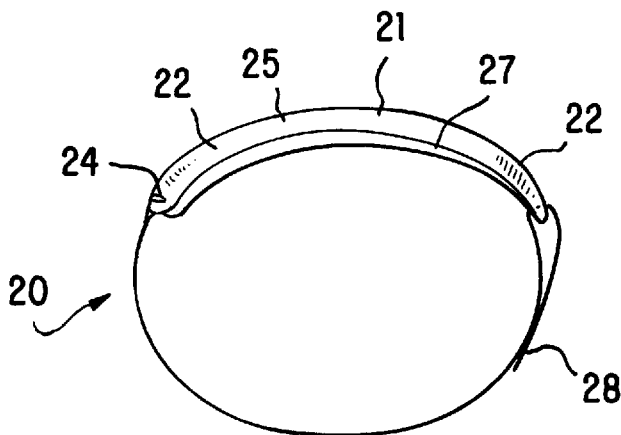
FIG. 3(a) is a top view of the band of FIG. 2.
Figure 8:
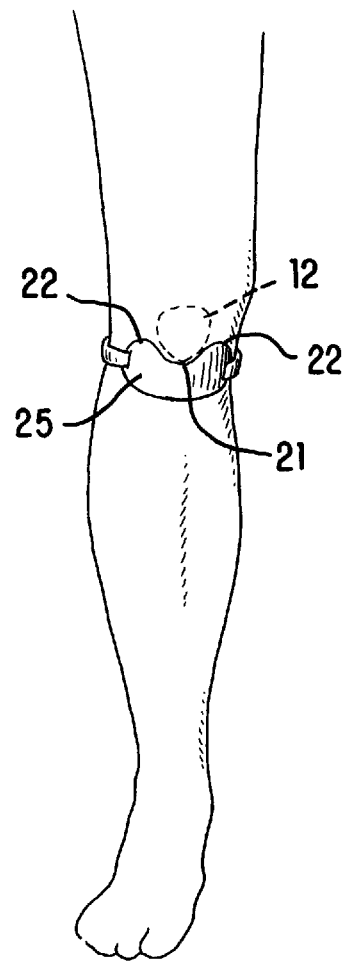
FIG. 8 is an anterior view of a leg with the band of the present invention positioned to compress the soft tissue overlying the femoral condyles.

FIG. 2 is a perspective view of the band of the present invention. The band, generally indicated at the numeral 20, has a "bowtie-shaped" symmetric compressive member or portion 25 which has an upper edge 30 having a generally parabolic notch therein and two superiorly projecting apices generally designated as 22 and seen more clearly in FIG. 3, and a saddle-like waist or mid-portion indicated at 21. The sides of the notch 21 have a point of inflection about midway between the base 21 of the notch and the apices 22. Two lines drawn tangent to the points of inflection will preferably intersect at an angle between 60°–120°. The compressive member 25 is generally arcuate, conforming to the curvature of the anterior portion of the knee. The compressive member 25 is symmetric about a narrow waist in its mid-portion generally indicated at 21. The upper edge of the narrow mid-portion 21 of the compressive member 25 is designed to support the patella at its inferior margin. In use, the lower margin 23 of the compressive member 25 is positioned to buttress against the tibial tuberosity (not shown) while the narrow waist 21 straddles the patellar tendon to allow unimpeded excursions thereof. A compressible lining 27 preferably separates the compressive member 25, which is preferably a slightly flexible plastic, from the underlying skin. The compression portion 25 is held in position around the leg by means of a strap portion 26. The strap portion 26 (FIG. 2(a)) provides a means for positioning the compression portion 25 so that the upwardly projecting apices 22 on the upper edge of the compression portion 25 exert symmetric inward pressure on the medial and lateral retinaculum 16 and 17, respectively, at the points designated by the broad arrows A in FIG. 1 and also hold the compression portion 25 in position. The strap portion 26 has a free end 28 which is brought through a slot 22 in the compressive member 25 and joined to itself by attachment means 29 such as, for example, Velcro® as shown in FIG. 2(a). An optional compressible foam or rubber pad 26a with a narrow waist and wide ends may be placed between the strap 26 and the skin for additional comfort. The compressive member 25 is symmetric laterally with respect to the midline notch 21 and is arcuate to conform to the anterior curvature of the knee as shown in FIG. 3(a), and the compressible lining 27 can have a non-uniform thickness.

Figure 4:
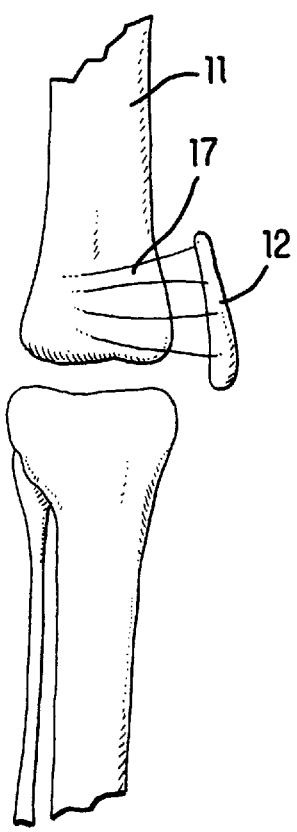
FIG. 4 is a lateral view of the bones of the leg showing the position of the soft tissue connected to the patella with respect to the femoral condyle when the leg is fully extended.
Figure 5:
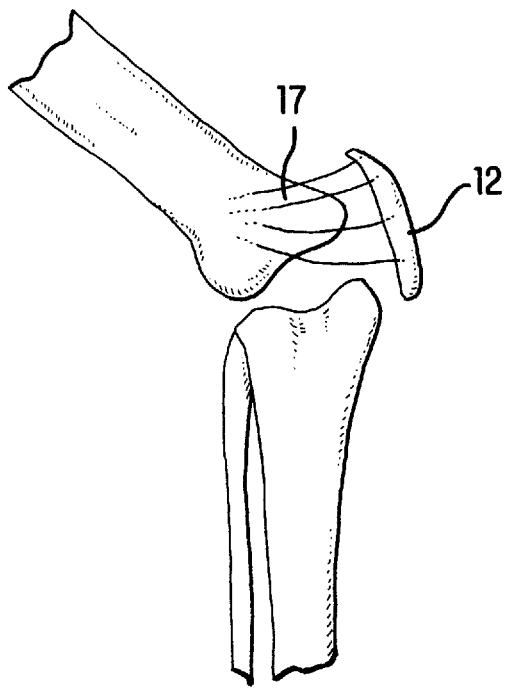
FIG. 5 is a lateral view of the bones of the leg showing the position of the soft tissue connected to the patella with respect to the femoral condyle when the leg is partially flexed.

Turning now to FIGS. 4 and 5, we see the position of the patella 12 with respect to the lateral femoral condyle 11 during extension (FIG. 4) and flexion (FIG. 5). The soft tissue comprising the lateral patellar retinaculum 17 slides across the margin of the femoral condyle. The soft tissue extends from the patella around the edge of the femoral condyle. Whenever there is irritation of the soft tissue, the soft tissue hangs up and snags on the edge of the femoral condyle on one or both sides. As motion of the leg continues, the snagged tissue stretches, then releases suddenly, causing the knee to give out. By compressing the medial and lateral retinaculum, the deceleration/acceleration forces in this snagged tissue are dampened, so that it no longer snaps, and "bowstrings" as it releases. With chondromalacia patella and patellar tendonitis, arthritis, synovitis, growing pains, Osgood Schlatter or other inflammatory condition of the retinaculum, by compressing the retinaculum where it slides across the margin of the femoral condyle during flexion or extension, the snapping of the soft tissue which serves to aggravate the underlying inflammatory condition and cause mechanical symptoms is reduced. Mechanical compression of the inflamed soft tissue while the tissue is in motion also serves to pump fluids out of the tissue thereby reducing swelling.

The knee operates in a vacuum. When the knee is spontaneously flexed and extended the vacuum increases before the tissues start to move. By symmetrically compressing the sliding soft tissue against the knee in the focal manner described herein, it may be possible to actually increase the interarticular pressures so that the tendency of the tissues to hang up is lessened. The overall local vacuum phenomenon is therefore reduced. The vacuum phenomenon is potentiated whenever there is inflammation because the tissues adjacent to each other tend to stick together like Velcro® pads when there is inflammation.

The position of the patella is not what's being affected by the strap of the present invention, but rather the tissue that rides over the femoral condyles during flexion and extension is compressed. That is, pressure on these tissues holds the tissue firmly against the femoral condyle and prevents it from snapping in the event it snags on the femoral condyle. The snapping, which causes microtrauma to the tissue, due to the rapid acceleration and deceleration of the affected tissue, causes and aggravates inflammation.

Figure 6:
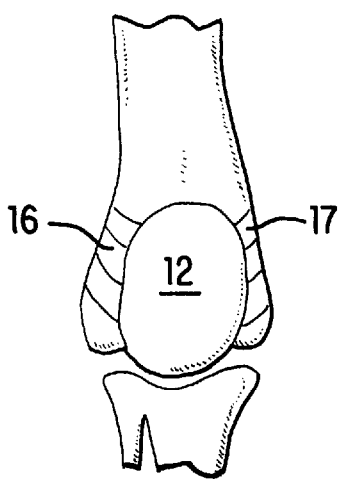
FIG. 6 is an anterior view of the knee fully extended.
Figure 7:
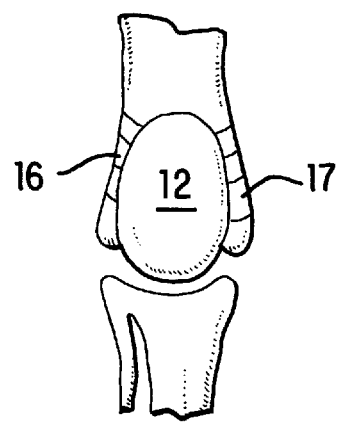
FIG. 7 is an anterior view of the knee partially flexed.

An anterior view of the knee of FIGS. 4 and 5 is shown in FIGS. 6 and 7. During inflammation, the folds of the extensor soft tissue 16 and 17 that come around from the medial and lateral sides of the knee, to the inferior margin of the patella and the fat pad in the front of the knee joint, slide over the medial and lateral margins of the femoral condyle 11 like a windshield wiper across a windshield. Because there is inflammation present in the soft tissue, any subtle changes in the profile of the femoral margins is accentuated during motion. This is because there is inflammation-associated capillary buds, all having nerve endings, on these tissues and also on the edge of the bone. These capillary buds impede the natural lubrication of the bone-soft tissue interface, so that they tend to stick and hang up more rapidly. Whenever there is inflammation, they tend to accelerate and then decelerate much more suddenly causing the attachment tissue, which is the anterior fat pad, to pull in underneath the kneecap and into the front of the knee joint which causes the joint to give way. That tissue, in turn, becomes bruised and irritated and sensitive because it is now getting caught inside the knee. This condition is most evident when a person has been sitting for a while, or in the morning, when these inflamed tissues have become slightly adherent together. Under these conditions, the normal vacuum phenomenon which occurs in all joints and is normal under most circumstances, is accentuated because the tissues don't move as easily. In response to the "sticky" tissue, when motion is attempted the vacuum increases and the tissues tend to get pulled into the knee joint. The two upwardly projecting apices 22 on the compression portion 25 of the band, which apices 21 are symmetrically spaced or positioned on either side of the notch 21, act as shock absorbers for the extensor folds as they slide over the margins of the femoral condyle on either side of the knee. The pressure brought to bear on the tissue decreases the tendency for the tissue to accelerate and decelerate, thereby relieving the snapping the sensation. By compressing specifically on these two folds, it may help to alleviate the accentuation of interarticular vacuum phenomenon at the beginning of motion.

The design of the present band is such that when it is properly positioned over the knee, it straddles the patellar tendon. By straddling the patellar tendon, it allows the normal freedom of elevation of the patellar tendon during motion of the knee joint. The compressive plate also abuts the tibial tuberosity, which helps to hold it in place, and helps the camming effect of the two superior projections of the compression plate. The device may be viewed as a cam action shock absorber for the extensor synovial soft tissue of the knee. The pad that goes around the posterior aspect of the knee has been designed to allow the knee to flex and extend in an unimpeded manner. The pad may, in itself, benefit the knee by focal compression of the medial and lateral posterior corners of the knee joint. The increased width of the pad localizes the medial and lateral corners of the knee where the hamstring tendons insert. This is seen more clearly in the series of lateral views of the knee in various stages of flexion shown in FIG. 9 through FIG. 12.

Figure 9A:
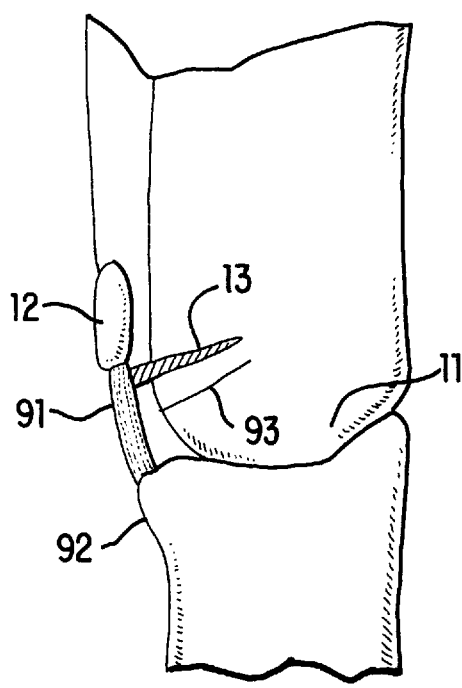
FIG. 9(a) is a lateral schematic view of a knee in a fully extended position.
Figure 10A:
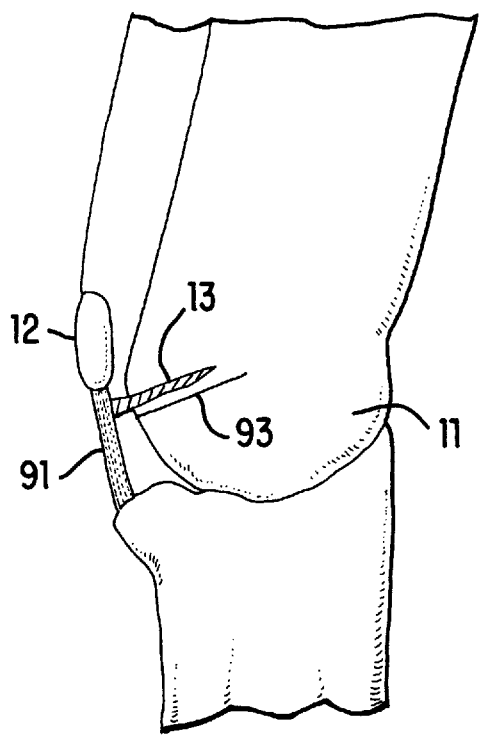
FIG. 10(a) is a lateral schematic view of a knee slightly flexed.
Figure 10B:
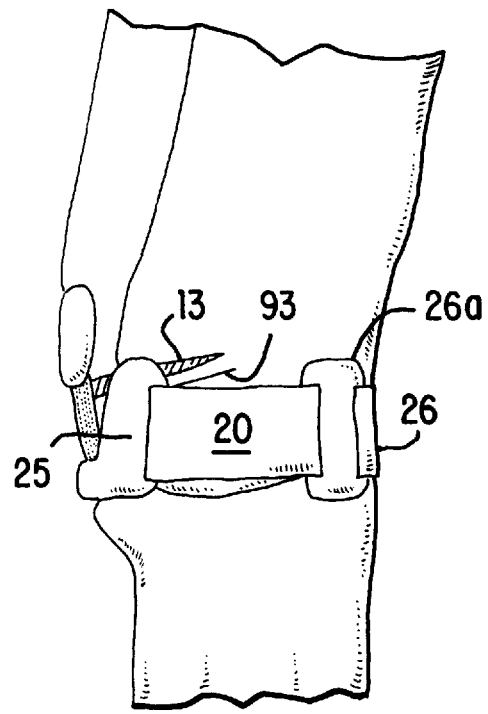
FIG. 10(b) is a lateral schematic view of a knee slightly flexed with the band of the present invention positioned to apply pressure to the synovial tissue lateral and posterior to the patella.

FIG. 9(a) is a schematic drawing showing the position of the patella 12, patellar tendon 91, and tibial tuberosity 92 and the lateral synovial fold 13 relative to a notch 93 on the femoral condyle 11. As flexion begins, the synovial fold 13 comprising soft tissue, slides across the femoral condyle 11 until it encounters a notch 93 or similar discontinuity on the surface of the condyle 11 as shown in FIG. 10(a). With further flexion, the synovial fold 13 snags on the notch 93, thereby stretching it as shown in FIG. 11(a). With continued flexion, the snagged tissue releases the notch and "bowstrings," or rapidly accelerates and decelerates to an equilibrium position shown in FIG. 12(a). Such acceleration/deceleration leads to microtrauma of the soft sinovial tissue and subsequent inflammation.

Figure 9B:
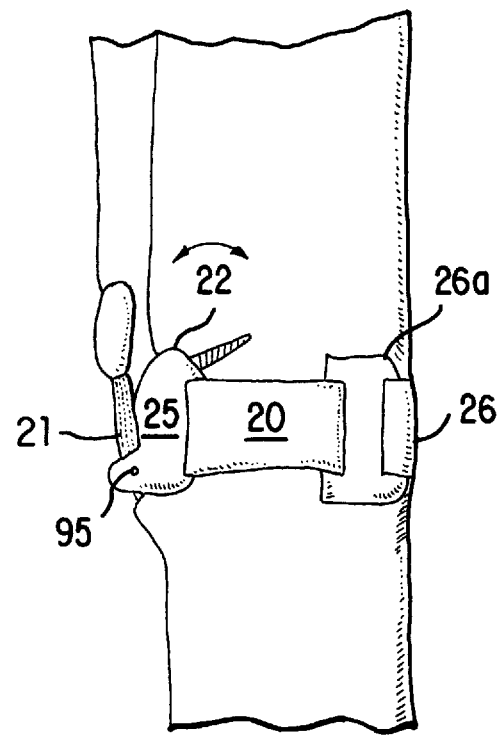
FIG. 9(b) is a lateral schematic view of a knee in a fully extended position with the band of the present invention positioned to apply pressure to the synovial tissue lateral and posterior to the patella.

FIG. 9(b) shows the knee joint as in 9(a) with the band 20 of the present invention positioned over the knee. The compressive member 25 of the band 20 is arcuate, being concave on the side facing the knee. The patellar tendon 91 rides through the notch 21 in the upper edge of the compressive member. An imaginary point 95 defines an axis through the compressive member around which the compressive member tilts or rotates when the knee is flexed. The rotation, which is generally in the direction of the double-headed arrow in FIG. 9(b), causes the apices or upward projecting portion 22 of the compressive member 25 to slidingly and symmetrically compress the underlying retinaculum and synovial tissue during flexion and extension of the knee thereby pumping fluids out of the tissue to reduce swelling.

The apices 22 of the compression portion 25 also apply selective focused eccentric compression to the medial and lateral anterior synovial folds 13 of the knee. The notch 21, or "isthmus," of the compressive portion 25 permits the compressive member to cam on its rotation axis 95 near the base or lower margin 23 of the compressive member 25 to effect focal compression of the medial and lateral compartments. With the band 20 in position, as the knee is progressively flexed as shown in FIG. 9(b) through FIG. 12(b), the synovial tissue is held against the condyle 11 during its traversal of the margin. This pressure prevents the snapping or "bowstringing" of the snagged tissue when it releases, thereby reducing microtrauma associated with rapid acceleration and deceleration of the tissue and undesirable sequellae such as inflammation and scar tissue formation.

While particular embodiments of the present invention have been illustrated and described, it would be obvious to those skilled in the art that various other changes and modifications can be made without departing from the spirit and scope of the invention. For example, bubbles or inflatable members may be positioned to selectively compress the soft synovial tissue underlying the medial and lateral patellar retinaculum to accomplish much of the shock absorption provided by the preferred embodiment described above. It is therefore intended to cover in the appended claims all such changes and modification that are within the scope of this invention.

What I claim is:

1. A method of treating medical conditions affecting the knee characterized by inflammation of the soft tissue of the knee comprising the symmetric and simultaneous application of compression to the medial and lateral patellar retinaculum without compressing the patella, wherein said symmetric and simultaneous application of compression to the medical and lateral patellar retinaculum is applied by a compressive band constructed from a slightly flexible plastic material and wherein said compressive band is adapted to fit between a tibial tuberosity and a patella of said knee.

2. The method of claim 1 wherein said medical condition is selected from the group consisting of arthritis, synovitis, tendonitis, chondromalacia patella, growing pain and Osgood-Schlatter disease.

3. A device adapted to releasably encircle a knee for treating symptoms associated with inflamed soft tissue of said knee, said knee comprising a tibial tuberosity and a patella, said tibial tuberosity being inferior to and separated from said patella by a distance and connected thereto by a patellar ligament, said knee further comprising retinaculum adjacent to and abutting said patella medially and laterally thereto, said device comprising:

(a) a planar, semi-rigid and elastically deformable compression plate having a concave posterior surface, a greatest length bisected by a midline perpendicular thereto and a least width and wherein said compression plate is symmetric with respect to said midline and wherein said compression plate is sized such that it is adapted to fit with its least width between said tibial tuberosity and said patella; and (b) a strap portion affixed to at least one side of said compression plate dimensioned to at least encircle a patient's leg at the knee and means thereon for affixing said strap portion around the knee.

4. The device in accordance with claim 3 wherein when encircling said knee, a portion of said compression plate, medial and lateral to said midline, applies greater pressure to said medial and lateral retinaculum than to other tissue of said knee.

5. The device in accordance with claim 3 further comprising a compressible portion affixed to said concave surface of said compression plate.

6. The device of claim 5 wherein said compressible portion has a non-uniform thickness.

* * * * *